(12) United States Patent
Lorusso et al.

(10) Patent No.: US 6,930,308 B1
(45) Date of Patent: Aug. 16, 2005

(54) SEM PROFILE AND SURFACE RECONSTRUCTION USING MULTIPLE DATA SETS

(75) Inventors: Gian Francesco Lorusso, Fremont, CA (US); Robert Anthony Watts, Folsom, CA (US); Alexander Jozef Gubbens, Redwood City, CA (US); Laurence Stuart Hordon, Santa Clara, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/265,520

(22) Filed: Oct. 3, 2002

Related U.S. Application Data (60) Provisional application No. 60/395,848, filed on Jul. 11, 2002.

(51) Int. Cl.[7] ............................................. G01N 23/00
(52) U.S. Cl. ..................... 250/310; 250/306; 250/307
(58) Field of Search ................................ 250/306, 307, 250/310, 396 R, 399, 397, 396 ML (56) References Cited

U.S. PATENT DOCUMENTS

| | | | | |
|---|---|---|---|---|
| 3,702,398 | A * | 11/1972 | Van-Essen et al. | 250/310 |
| 4,818,874 | A * | 4/1989 | Ishikawa | 250/310 |
| 5,212,383 | A * | 5/1993 | Scharf | 250/310 |
| 5,877,498 | A | 3/1999 | Sugimoto et al. | |
| 5,949,901 | A | 9/1999 | Nichani et al. | |
| 6,118,540 | A | 9/2000 | Roy et al. | |
| 6,157,032 | A * | 12/2000 | Into | 250/310 |
| 6,184,975 | B1 * | 2/2001 | Henstra et al. | 356/123 |
| 6,201,240 | B1 | 3/2001 | Dotan et al. | |
| 6,298,149 | B1 | 10/2001 | Nichani et al. | |
| 6,300,629 | B1 | 10/2001 | Lawrence | |
| 6,353,222 | B1 * | 3/2002 | Dotan | 250/310 |
| 6,472,662 | B1 * | 10/2002 | Archie | 250/307 |

(Continued)

FOREIGN PATENT DOCUMENTS

| | | |
|---|---|---|
| WO | WO 00/70646 | 11/2000 |

(Continued)

OTHER PUBLICATIONS

Wei, et al., "Intensity-and Gradient-Based Stereo Matching Using Hierarchical Gaussian Basis Functions", IEEE Transactions on Pattern Analysis and Machine Intelligence, vol. 20, No. 11, Nov. 1998, pp. 1143-1160.

(Continued)

*Primary Examiner*—Nikita Wells
*Assistant Examiner*—Christopher M. Kalivoda
(74) *Attorney, Agent, or Firm*—Beyer, Weaver & Thomas, LLP.

(57) ABSTRACT

A highly accurate technique for inspecting semiconductor devices is described. The technique involves utilizing multiple sets of measurement data obtained by a scanning electron microscope (SEM) to determine the dimensional parameters of a semiconductor device. The SEM collects each set of data from a different angular orientation with respect to the device. The dimensional parameters of the semiconductor device are determined by analyzing the relationship between the SEM inspection angle and the collected data sets. Various configurations of an SEM can be used to implement this invention. For instance an electron beam inspection system of the present invention can have at least two sets of deflectors for guiding the electron beam, a swiveling specimen stage, and/or a set of detectors set about the specimen at different angular orientations.

12 Claims, 11 Drawing Sheets

U.S. PATENT DOCUMENTS 6,521,891 B1 * 2/2003 Dotan et al. ................. 250/310
6,525,328 B1 * 2/2003 Miyoshi et al. ......... 250/492.22
6,614,026 B1 * 9/2003 Adamec ..................... 250/398

FOREIGN PATENT DOCUMENTS

WO      WO 01/45136      6/2001

OTHER PUBLICATIONS

Komatsu, et al., "Measurement of geometrical dimensions using scanning electron microscopy", Japanese Society of Electron Microscopy, Journal of Electron Microscopy, vol. 48, No. 4, 1999, pp. 407-415.

* cited by examiner

SEM PROFILE AND SURFACE RECONSTRUCTION USING MULTIPLE DATA SETS

CROSS REFERENCE TO RELATED APPLICATIONS

This application claims priority of U.S. Provisional Patent Application No. 60/395,848, filed Jul. 11, 2002, which application is incorporated herein by reference in its entirety for all purposes.

FIELD OF THE INVENTION

The present invention relates generally to semiconductor inspection techniques, and more specifically to inspection techniques that utilize multiple sets of data gathered from different positions about a semiconductor specimen.

BACKGROUND OF THE INVENTION

The industry of semiconductor manufacturing involves highly complex techniques for integrating circuits within semiconductor materials. Due to the large scale of circuit integration and the decreasing size of semiconductor devices, the semiconductor manufacturing process is prone to processing defects. Inspection procedures are therefore critical to maintain quality control. Since the inspection techniques play an integral and significant part of the manufacturing process, the semiconductor industry constantly seeks more accurate and efficient testing procedures.

Figure 1:
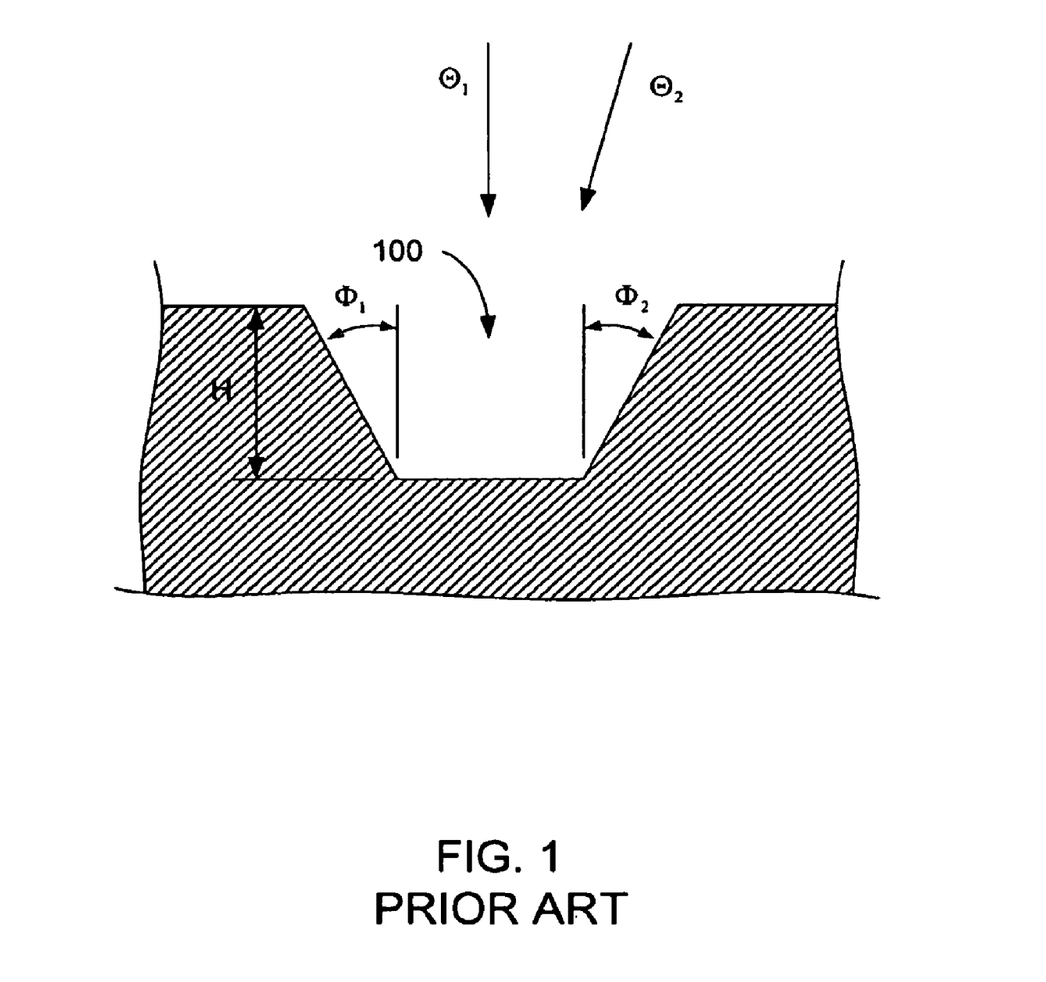
FIG. 1 illustrates a side plan, cross-sectional view a trench feature inspected by stereoscopic reconstruction.

One type of inspection technique determines three-dimensional parameters of features within an integrated circuit device. For instance, such techniques can measure the height and sidewall angles of a trench pathway or the depth and sidewall slope of a contact via. One such technique referred to as stereoscopic reconstruction uses a scanning electron microscope (SEM) that obtains two separate images or line scans of a semiconductor feature. Each of the two images or line scans is obtained while the SEM is directed at the semiconductor feature in a unique incident angle. Each image or line scan is a different data set since the electron beam hits the feature at a different angle. The three-dimensional characteristics of the feature are determined by using elementary geometry. FIG. 1 illustrates a side plan, cross-sectional view a trench feature 100 inspected by stereoscopic reconstruction. $\theta_1$ and $\theta_2$ indicate the two incident angles at which each of the two images are taken; H represents the height of trench 100; and $\phi_1$ and $\phi_2$ represent each of the sidewall angles. Since only two sets of data are available, a simple trapezoid is constructed to approximate the feature under investigation. Unfortunately, such a simple technique typically produces estimations having poor precision and accuracy. Estimations generated by this technique can be useful when deviation from a process rather than absolute numbers is required, such as in a production environment. However, many processes require more accurate and detailed feature parameter information thereby revealing limitations of stereoscopic inspection.

Metrology atomic force microscope (AFM) is another inspection technique for determining feature parameter information. However, this is not reliable because the tip convolution is difficult to use and is much slower than SEM techniques. A destructive technique of focused ion beam (FIB) cross-sections is available, however, destructive techniques are less appealing due to its inherent requirement of rendering specimens useless.

In view of the foregoing, an inspection technique capable of accurately estimating detailed semiconductor feature information would be desirable.

BRIEF SUMMARY OF THE INVENTION

The present invention is directed to an inspection technique capable of accurately estimating detailed three-dimensional semiconductor feature information.

One aspect of the present invention pertains to an apparatus for inspecting a semiconductor specimen. The apparatus includes an electron beam device that directs an electron beam onto the semiconductor specimen, an electron beam column having a central axis, wherein the electron beam travels along the central axis until the electron beam becomes incident with the specimen, a first quadrapole configured to deflect the electron beam, a second quadrapole configured to deflect the electron beam, and a magnetic lens configured to focus the electron beam upon the specimen.

Another aspect of the present invention pertains to a method for inspecting the surface of a semiconductor specimen. This method involves directing an electron beam along a central axis and towards the semiconductor specimen, securing the semiconductor specimen in a stationary position, deflecting the electron beam away from the central axis, and deflecting the electron beam back towards the central axis such that the electron beam is incident within a specific area on the semiconductor specimen regardless of the incident angle of the electron beam.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

Generally, the present invention relates to a highly accurate technique for inspecting semiconductor devices. The inventive technique involves utilizing multiple sets of measurement data obtained by a scanning electron microscope (SEM) to determine the three-dimensional parameters of a semiconductor device. We define here a set of measurement data as an SEM image or scan. The SEM will collect each set of measurement data at a different angular orientation. The three-dimensional parameters of the semiconductor device are determined by analyzing the relationship between the angle at which measurements are gathered and the measurements themselves. In other words, by using geometrical calculations, the three-dimensional shape of a specimen can be determined from the various sets of measurements. Appropriate computer vision techniques can be used to complete these measurements. The estimated parameters can be used to "reconstruct" a model of the device. Useful information would provide dimensions to features on a semiconductor device such as contact pads, contact vias, trenches, etc. In addition to providing highly precise inspection information, the inventive technique does not require the destruction of an inspected specimen, as it happens with other analytical techniques such as FIB.

The accuracy of the inventive technique stems from the use of at least three different sets of inspection data. The accuracy of measured dimensional parameters increases when high numbers of data sets are utilized. The use of multiple sets of information for the same specimen is sometimes referred to as "information redundancy." The inventive method produces a better and more detailed approximation of the features on a semiconductor specimen than stereoscopic techniques that use only two sets of data (see FIG. 1). As will be described below, various configurations of SEM devices can be used to obtain these multiple data sets. The analysis techniques used for this invention can be embodied and automated with software based upon computer vision techniques.

An inspection apparatus appropriate for implementing the current invention should be capable of measuring the features of a semiconductor device at a high resolution. One such apparatus is a scanning electron microscope (SEM). Furthermore, the inspection apparatus is required to take measurements of a semiconductor device from at least three different inspection angles.

An inspection apparatus of the present invention can be configured in a variety of manners to have the capability to measure a specimen from different inspection angles. Preferably, the inspection apparatus is constructed so that large amounts of data can be collected with minimal effort. One such inspection apparatus design involves tilting the electron beam such that the inspected location on the specimen does not change when the incident angle is changed. With respect to an SEM, this capability can be achieved with an electron beam device that "rocks" the electron beam by using a properly designed double deflection technique. For instance, two sets of deflection devices, electrostatic and/or magnetic, can be used.

Figure 14A:
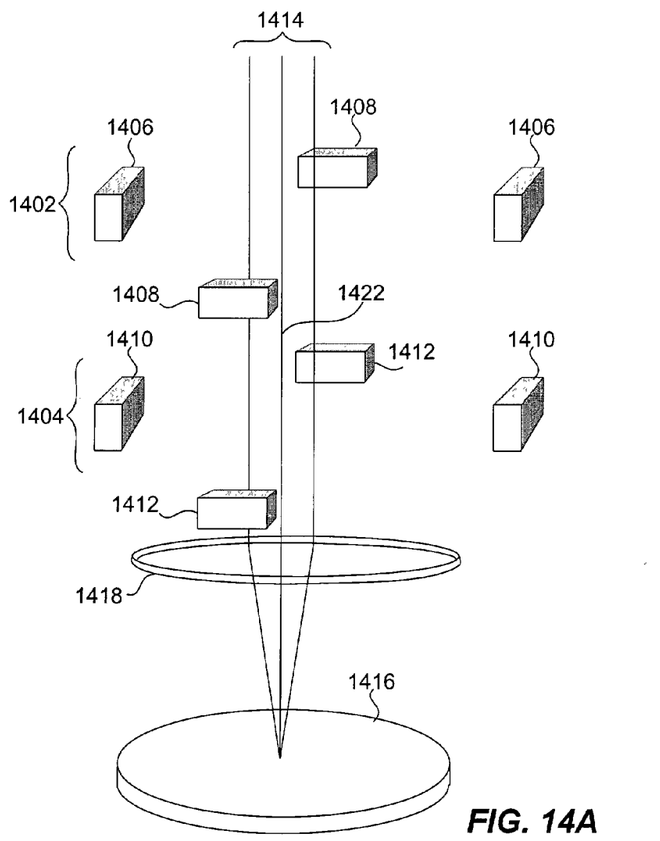
FIGS. 14A and 14B illustrate partial, perspective views of an electron beam device that utilizes two deflectors, according to one embodiment of the present invention.
Figure 14B:
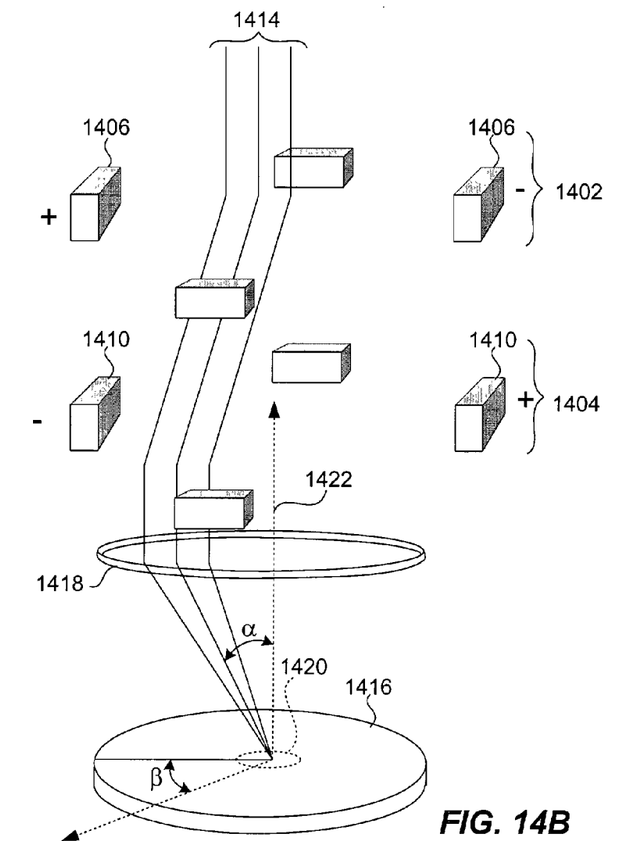

FIGS. 14A and 14B illustrate partial, perspective views of an electron beam device 1400 that utilizes two sets of electrostatic deflectors 1402 and 1404, according to one embodiment of the present invention. Deflectors 1402 and 1404 are opposing sets of electrical charge carrying poles set along perpendicular axes. Deflector 1402 has opposing sets of poles 1406 and 1408 and deflector 1404 has opposing sets of poles 1410 and 1412. Deflectors 1402 and 1404 are positioned along the path that the electron beam takes on its way to specimen 1416. Each of the opposing sets of poles 1406 and 1408 sandwich the electron beam 1414 such that when opposing electrical voltages are applied to a deflector 1402 or 1404, the path of electron beam 1414 can be deflected. Deflectors 1402 and 1404 are positioned to deflect electron beam 1414 in orthogonal directions. For example, electron beam 1414 can be deflected along an x and a y-axis. By charging each of the deflectors in each of the perpendicular directions, electron beam 1414 can be deflected at various angles in an x-y plane as it passes through deflectors 1402 and 1404. In other embodiments, deflectors 1402 and 1404 can be positioned to deflect electron beam 1414 in various directions that do not necessarily have to be in orthogonal directions. For example, opposing sets of poles can be arranged at various positions about the perimeter of the electron beam.

Magnetic lens 1418 is positioned below the lower deflector 1404 and operates to focus electron beam 1414 so that electron beam 1414 hits specimen 1416 within a discrete area 1420.

FIG. 14A illustrates a scenario where no electrical voltage is applied to deflectors 1402 and 1404 so that electron beam 1414 follows a straight path down to specimen 1416. On the other hand, FIG. 14B illustrates a scenario where opposing electrical voltages are applied to each set of poles 1406 and 1410. In deflector 1402, a negative voltage is applied to the pole 1406 on the right hand side, while in deflector 1404, a negative voltage is applied to the pole 1410 on the left-hand side. This arrangement of electrical voltages causes electron beam 1414 to bend towards the positive pole within deflector 1402 and therefore away from the central axis of the electron beam path 1422. Then, as the electron beam passes through deflector 1404, electron beam 1414 is deflected towards the positive pole within the set of poles 1410 and therefore back towards the central axis 1422. After passing through magnetic lens 1418, electron beam 1414 hits specimen 1416 in area 1420 at an incident angle alpha. Note that in FIG. 14B, only poles within one of the orthogonal directions were charged so that electron beam 1414 is deflected in a single plane. In alternative embodiments, electrical charge can also be applied to sets of poles 1408 and 1412 so that electron beam 1414 is also deflected in the orthogonal direction. By using a combination of electrical charges within orthogonal directions, deflectors 1402 and 1404 are able to deflect electron beam 1414 away from and then back towards the central axis 1422 at various angles. This allows electron beam 1414 to be incident with specimen 1416 at various angles defined by alpha and beta.

Quadrapoles 1402 and 1404 can deflect electron beam 1414 so that it is incident upon the same point or approximately the same point of specimen 1416 while landing at various incident angles. As shown in FIG. 14B, electron beam 1414 is incident with specimen 1416 within discrete area 1420. As mentioned earlier, this is advantageous as a single area of specimen 1416 can be inspected at various inspection angles without repositioning specimen 1416 for each inspection angle as is typically required. In other words, specimen 1416 can be held in a stationary position throughout inspection processes at various angles. In contrast, current inspection systems bend the electron beam away from the central axis of the electron beam so that the beam lands at different areas on the specimen. Thus, physically repositioning the specimen and making the calculations required to implement the repositioning is required in order to inspect a single area on a specimen at different angles.

In alternative implementations, deflectors 1402 and 1404 can also deflect electron beam 1414 so that beam 1414 lands at various, but specified locations upon specimen 1416. For instance, electron beam 1414 can be made to hit the surface of specimen 1416 at locations other than area 1420. This capability allows for various portions of a specimen to be examined without moving the specimen with respect to the electron beam. At the same time, the angle of electron beam 1414 can be specified.

In other embodiments, additional sets of deflectors can be used to fine-tune the deflection of electron beam 1414. Not shown in FIGS. 14A and 14B are the charge carrying poles that are commonly used to scan electron beam 1414 along a path on specimen 1416. Since such poles are commonly used and well known in the art, description of such poles is not included within this specification.

Figure 2:
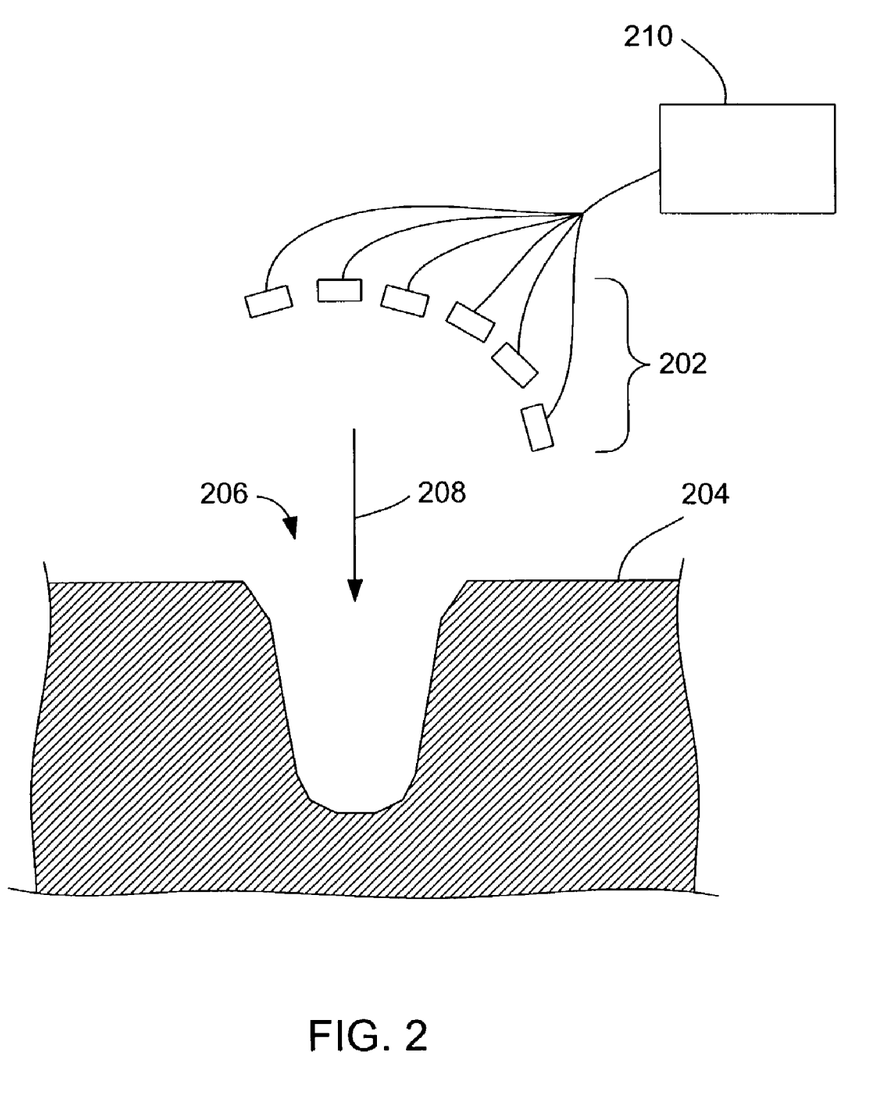
FIG. 2 illustrates an exemplary embodiment of an arrangement of detectors positioned above a semiconductor specimen.

Another SEM configuration for the current invention uses three or more detectors positioned about the specimen at different angular orientations so that each detector collects electrons emitted from the specimen at different angles. In this configuration, the electron beam can be directed at the specimen in a single orientation. The use of many more than three detectors provides for the collection of additional data sets that would increase the accuracy of the inspection system. FIG. 2 illustrates an exemplary embodiment of an arrangement of detectors 202 positioned above a semiconductor specimen 204. Each of detectors 202 is positioned at a different angular orientation with respect to specimen 204. Detectors 202 are attached to a computing system 210 that receives signals from each of detectors 202 and analyzes the data. Specimen 204 includes a trench 206 formed within its the surface. Arrow 208 represents the in-coming electron beam from the inspection SEM. In some embodiments of the inspection SEM, the arrangement of detectors can be shifted relative to the specimen to collect additional sets of data.

Another embodiment of the current invention uses an SEM configuration having a specimen stage that swivels so that the angle between the specimen and the electron beam can be adjusted for different sets of measurements. These various configurations described here can be implemented within an SEM individually or used in various combinations.

Figure 3:
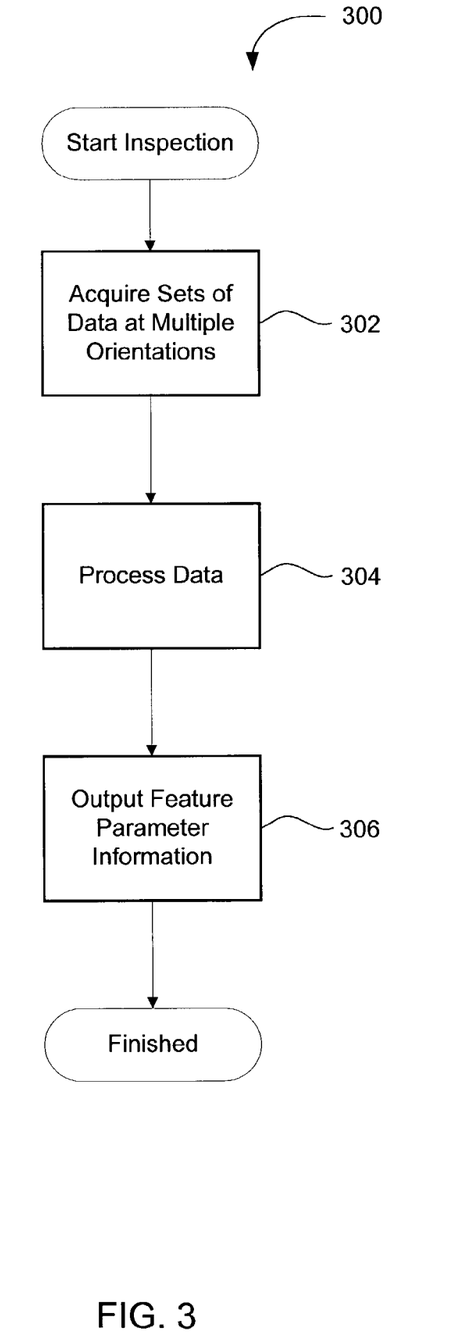
FIG. 3 illustrates a flow diagram, which describes the inspection technique according to one embodiment of the present invention.

The discussion will now describe the inspection technique of the present invention in more detail through the aid of flow diagrams. FIG. 3 illustrates a flow diagram 300, which describes the inspection technique according to one embodiment of the present invention. Flow diagram 300 starts at block 302 by acquiring sets of inspection data collected at multiple orientations about the specimen. For example, an SEM collects a single data set by scanning a specific area of a specimen and recording images or scans. At least three sets of data are collected. More than three sets of data are collected for higher accuracy of the final results. For example, hundreds of measurements at different angles can be used to obtain the dimensional parameters of the semiconductor device. Each SEM measurement contains a set of data that includes the intensity level of electrons emitted from the specimen and the location within the inspection system at which the scattered electrons are detected.

After data sets are collected in block 302, the technique proceeds to data processing in block 304. The data processing of block 304 can begin after all data has been completely collected or it can start shortly after data collection begins and continue to operate in parallel with the data collection. The information generated by data processing block 304 is output at block 306. In a similar manner, the outputting operations of block 306 can be performed after completion of block 304 operations and provide off-line inspection capabilities. Alternatively, the outputting of information of block 306 can operate in parallel with the data processing of block 304 to provide real-time inspection information. Inspection results include numerical results, 2-D, and 3-D images that represent the parameters of the inspected surface of the specimen.

Figure 4:
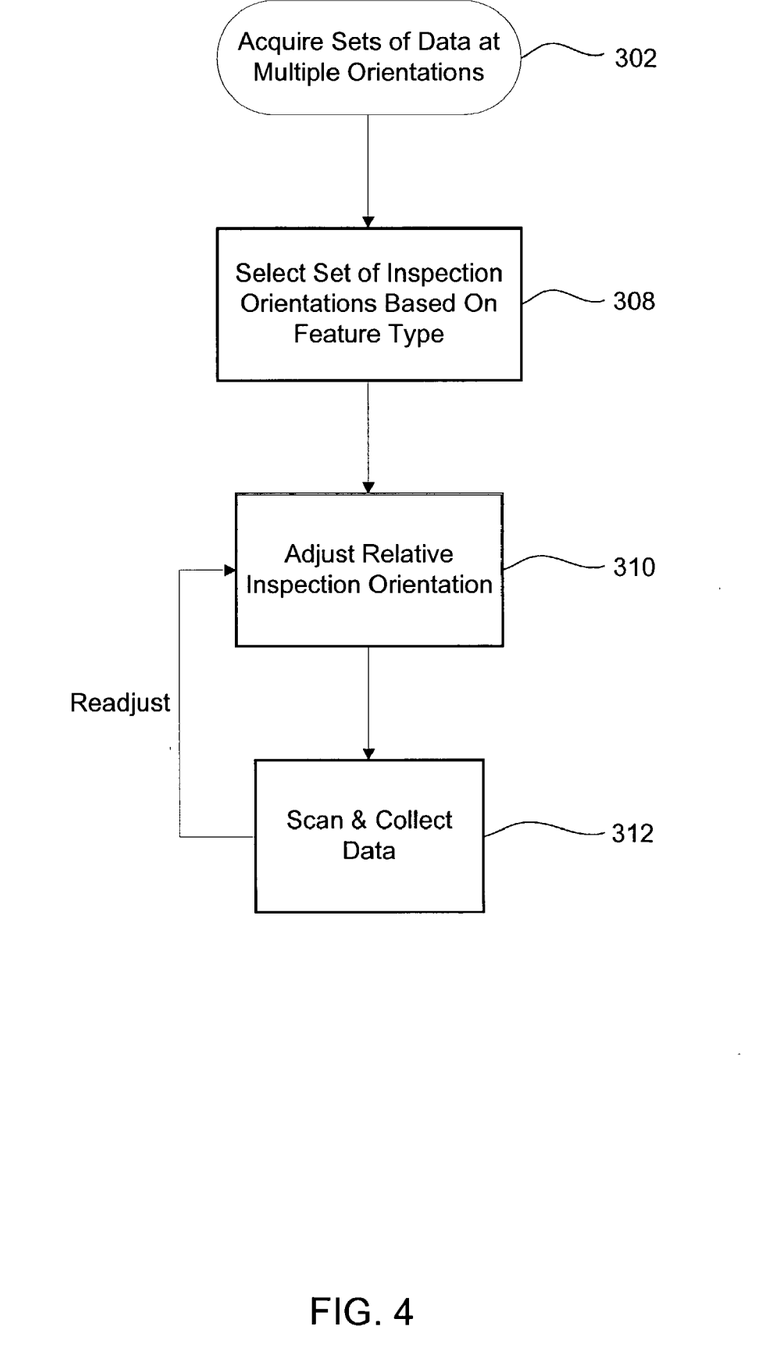
FIG. 4 illustrates the sub-operations of block 302 of FIG. 3 according to one implementation of the present invention.

FIG. 4 illustrates the sub-operations of block 302 of FIG. 3 according to one implementation of the present invention. The first sub-operation 308 for acquiring multiple data sets involves selecting a range of inspection orientations in which to obtain measurements of the specimen.

Figure 6:
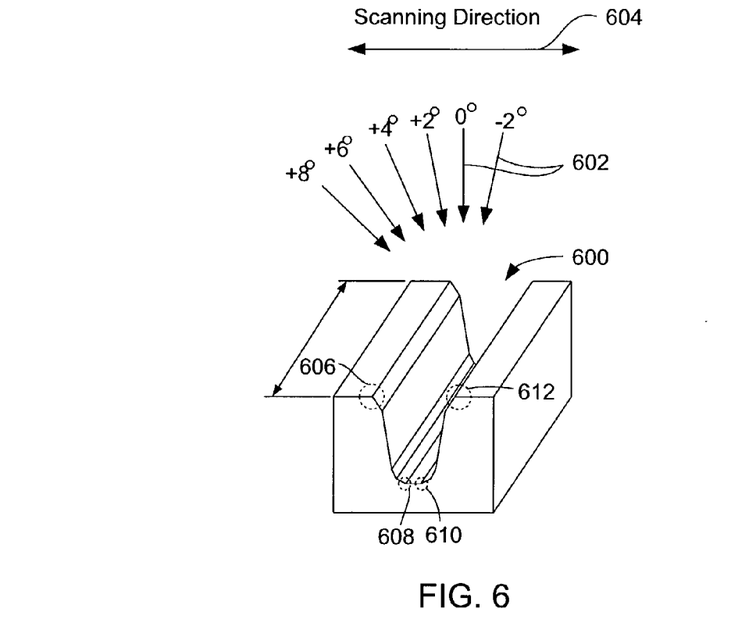
FIG. 6 illustrates a perspective, cut-away view of a trench within a semiconductor device and multiple inspection angles at which an electron beam can be scanned over the trench.
Figure 7:
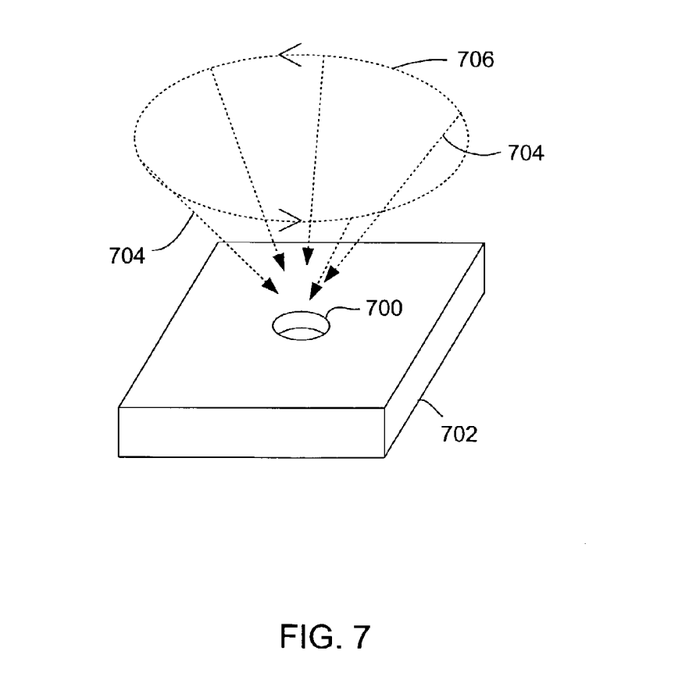
FIG. 7 illustrates a perspective view of a contact via within a semiconductor device and multiple inspection angles at which the electron beam is directed at contact via.

The range of orientations depends upon the feature types to be inspected. The range of inspection orientations should include angles in which the data sets vary from one another due to the change in the angle of the electron beam, though not every set of data must be completely different from the next. Through collecting such data, meaningful analysis is performed because the differences in values between each data set can be related to the dimensions of the inspected specimen. FIGS. 6 and 7 illustrate exemplary electron beam inspection strategies for inspecting a trench and a contact via, respectively, located within a semiconductor device.

Specifically, FIG. 6 illustrates a perspective, cut-away view of a trench 600 within a semiconductor device and multiple inspection angles 602 at which an electron beam can be scanned over trench 600. Scanning direction 604 describes the path along which the electron beam is scanned across the width of trench 600. In this case, because of the vertical symmetry of the trench, the optimal analysis algorithm involves scanning the electron beam in a perpendicular direction with respect to length the trench. During each scanning sweep over trench 600, electron beam is positioned in one of the inspection angles 602 and measures trench 600 from a different inspection angle. Note that taking measurements of trench 600 along a single scanning direction axis provides data to determine the profile for a single slice of trench 600. In order to fully determine the surface topology of trench 600, the electron beam should be raster scanned along the length of trench 600. In other words, combining the profile of multiple slices of trench 600 can form the surface topology for a section of trench 600.

FIG. 7 illustrates a perspective view of a contact via 700 within a semiconductor device 702 and multiple inspection angles 704 at which the electron beam is directed at contact via 700. In this case, the inspection angles 704 define a circular path 706 through which the electron beam travels. It is noted that various ranges of inspection angles, number of angles at which electrons can be detected, and scanning directions could be used to gather data concerning the semiconductor features of FIGS. 6 and 7. For instance, an inspection process could use hundreds of individual inspection angles to gather hundreds of sets of data for analysis. Also, the scanning direction 604 in FIG. 6 need not be exactly perpendicular to the lengthwise axis of trench 600 and circumference 706 defined in FIG. 7 can vary in size and shape (e.g., elliptical).

An alternative method of gathering data sets at each of the inspection angles involves a single electron beam directed at the feature of interest (e.g., a trench or a via) and a detector placed at each of the desired inspection angles.

After the range of inspection angles is selected for the feature or features to be inspected, actual scanning and data collection is iteratively performed in blocks 310 and 312 in FIG. 4. In block 310, the relative inspection angle is set. This could involve the adjustment of the angle of the electron beam, the adjustment of the position of the swiveling specimen stage, or the positioning of multiple detectors. Then in block 312, measurements from the set inspection orientation(s) are taken. Blocks 310 and 312 are repeated to measure the specimen from various inspection angles. For instance, block 310 is repeated to re-adjust the relative inspection angle by adjusting the voltage within deflectors as described in FIGS. 14A and 14B, rotating the specimen stage, or shifting a detector(s). For example, with respect to FIG. 6, an electron beam would be set at each of inspection angles 602 and scanned over trench 602 in scanning direction 604. Inspection angles 602 could for example, be set at +8, +6, +4, +2, 0, and –2 degrees. When multiple detectors are placed over the specimen, repeating block 310 can involve shifting the orientations of one or more of the detectors so that the detector(s) can collect data from a different inspection angle. However, repeating block 310 to shift detectors is not strictly necessary when three or more detectors are used since a sufficient number of measurements can be taken with the detectors in a single position. In case only one detector is used, the detector should be shifted to the various inspection angles for each measurement.

Figure 8:
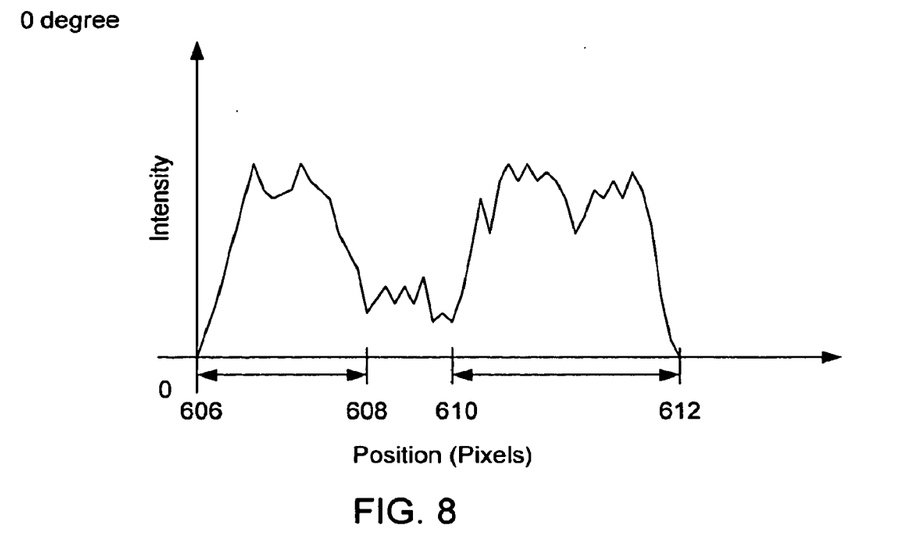
FIG. 8 represents data collected when the electron beam is positioned at 0 degrees with respect to a trench.
Figure 9:
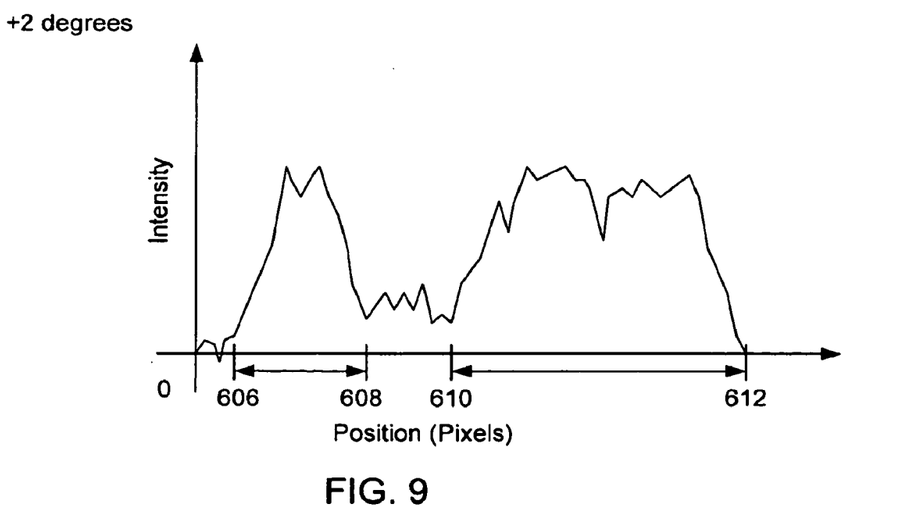
FIG. 9 illustrates the Intensity graph as the electron beam is scanned over trench while positioned at an orientation of −2 degrees.

FIGS. 8 and 9 illustrate exemplary measurement data collected by an SEM after scanning trench 600 of FIG. 6 at two different inspection angles. The data of FIGS. 8 and 9 are graphed on a coordinate system having a vertical axis representing the intensity of the electrons scattering from trench 600 and a horizontal axis representing the position within the inspection system at which the scattered electrons are detected. The position at which electrons are detected is measured in pixels. FIG. 8 represents data collected when the inspection orientation is 0 degrees with respect to the trench. In other words, at 0 degrees, the inspection angle is pointed directly downwards at the trench. The graph of the Intensity in FIG. 8 noticeably rises at the low and high ends of the Position axis while dipping in the middle range of the Position axis. The two high intensity portions of the Intensity graph correspond to the sidewalls of trench 600. Referring to both FIGS. 6 and 8, the left-hand side sidewall is located between points 606 and 608 and the right-hand side sidewall is located between points 610 and 612. The bottom of trench 606, between points 608 and 610, corresponds to the low intensity portion of the graph in FIG. 8. The specific intensity levels obtained is a result of the physics involved with electrons emitted from the surface of trench 600.

FIG. 9 illustrates the Intensity graph when the inspection angle is +2 degrees. At +2 degrees, the left-hand side sidewall appears narrower to SEM inspection system than at 0 degrees. Also, the right-hand side sidewall appears larger at +2 degrees. This represents itself in the Intensity graph of FIG. 9 through points 606 and 608 that are now closer together and through points 610 and 612 that are now farther apart.

Figure 5:
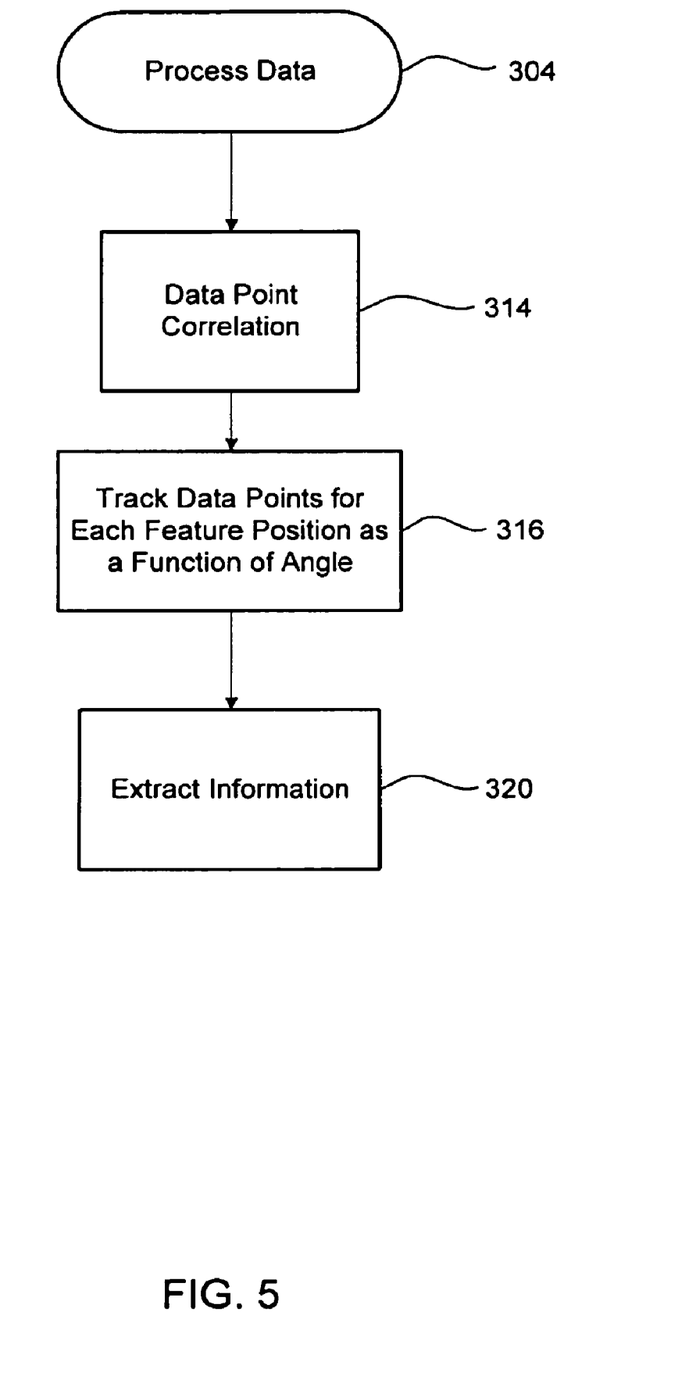
FIG. 5 describes the general algorithm used to process the data to generate information about the semiconductor specimen.
Figure 10:
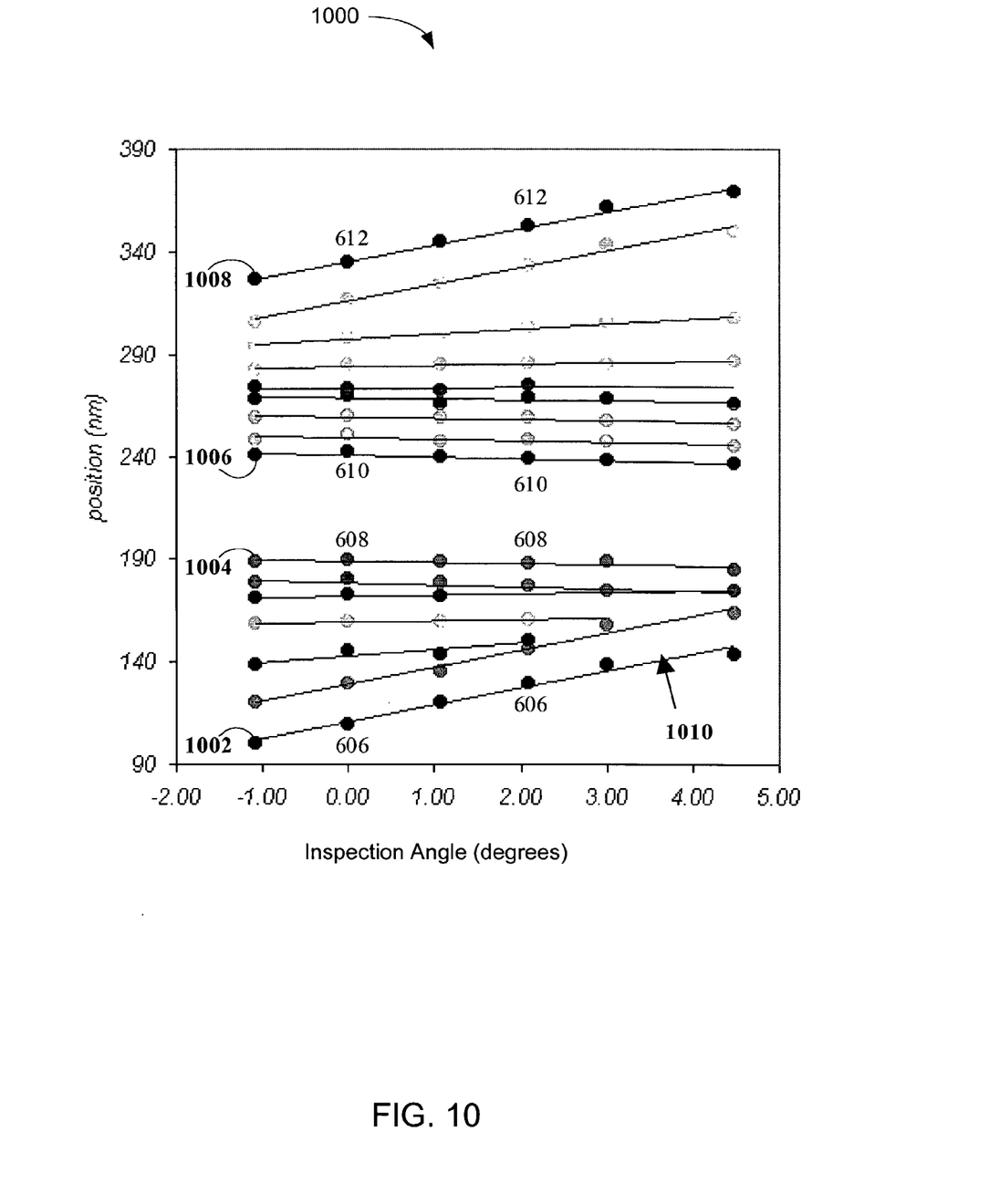
FIG. 10 illustrates the data points collected for a trench in a graph having a vertical axis for position in nanometers and a horizontal axis for the angular tilt of an electron beam.

FIG. 5 describes the sub-operations of block 304 for processing the measurement data to generate information about the semiconductor specimen. The first sub-operation represented in block 314 involves identifying data points from each measurement data set that correspond to the same point along the specimen that was inspected. For example, the data points from each data set that correspond to the top and bottom of the left hand-side sidewall are identified (606, 608 in FIGS. 8, 9). Also the data points from each data set that correspond to each point between the top and bottom of the right-hand side are identified (610, 612 in FIGS. 8, 9). This process of correlation is performed for all the data points that correspond to the various features of interest. FIG. 10 illustrates the data points collected for a trench in a graph 1000 having a vertical axis for position in nanometers and a horizontal axis for the angular tilt of the inspection angle. The data points corresponding to the data set obtained at each inspection angle are placed along their corresponding inspection angle axis in the graph 1000. Graph 1000 illustrates the data points taken for six sets of data. With respect to each data set within graph 1000, the data point with the lowest position corresponds to the top of the left-hand side sidewall and the data point with the highest position corresponds to the top of the right-hand side sidewall. Each of the data points in between the highest and lowest positions corresponds to a point within the trench. For example, with respect to trench 600 of FIG. 6, points 1002 and 1004 could correspond to the top and bottom of the left-hand side of the sidewall of trench 600, respectively, and points 1006 and 1008 could correspond to the bottom and top of the right-hand side sidewall of trench 600.

In block 316 of the flowchart in FIG. 5, the data point for each location within a feature is identified at each inspection angle. This means identifying one subset of data for each distinguishable location within the trench by using computer vision algorithms to correlate the data sets. As seen in FIG. 10, curve 1010 describes the position of the top of left-hand side sidewall 606 as a function of the inspection angle. The curves in graph 1000 show the trend of points 1002 and 1004 getting closer to each other and the points 1006 and 1008 getting farther apart as the inspection angle increases.

In block 320, algorithms taking advantage of geometrical relationships between the position and inspection angle of the data points can be used to generate information regarding the dimensional parameters of an inspected semiconductor feature. In other words, through the understanding of geometrical relationships, measurement data arranged in a graph such as in FIG. 10 can be analyzed to generate the dimensional measurements of a semiconductor specimen. In the specific case of FIG. 10, the three-dimensional information is analyzed by fitting each subset to a straight line.

Figure 11:
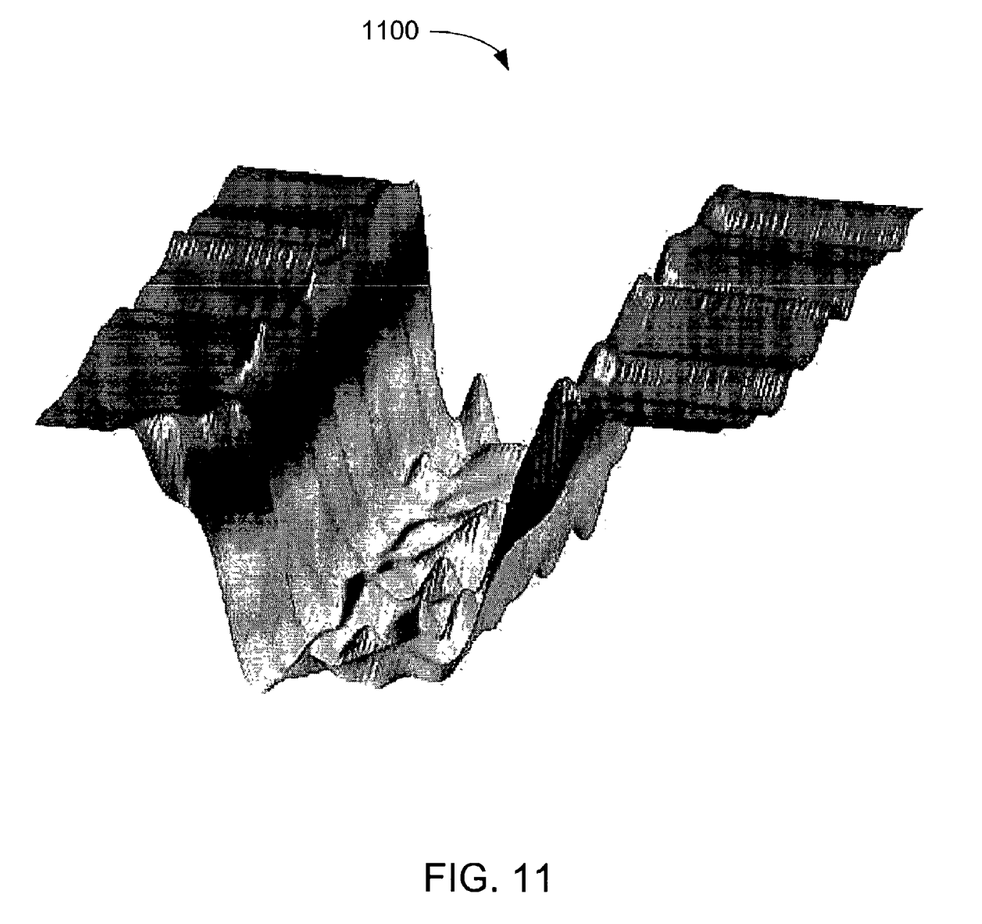
FIG. 11 illustrates a three-dimensional image of a semiconductor trench that is generated by the inventive technique.

The extracted parameters provide information about the feature in a variety of manners. For instance, a two-dimensional profile image of a cross-section of a feature or a three-dimensional image of a feature can be generated. FIG. 11 illustrates an exemplary three-dimensional image 1100 of a semiconductor trench generated by the inventive process.

Also, the approximations for the height, width, sidewall angles, etc. of a feature can be provided. Or, the average of such dimensions can be provided for a certain section of an inspected feature.

Computer System Embodiment

Figure 12:
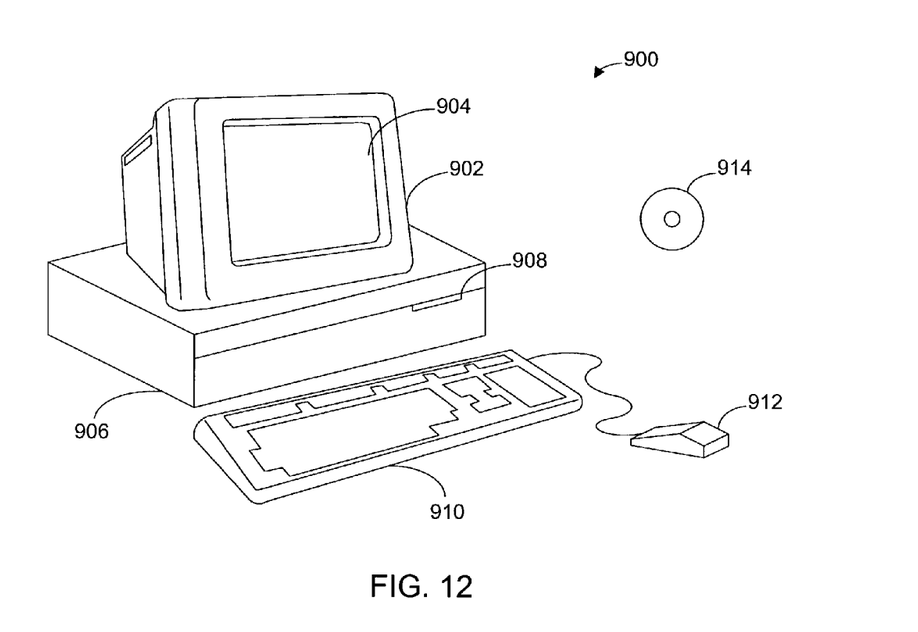
FIGS. 12 and 13 illustrate a computer system suitable for implementing embodiments of the present invention.
Figure 13:
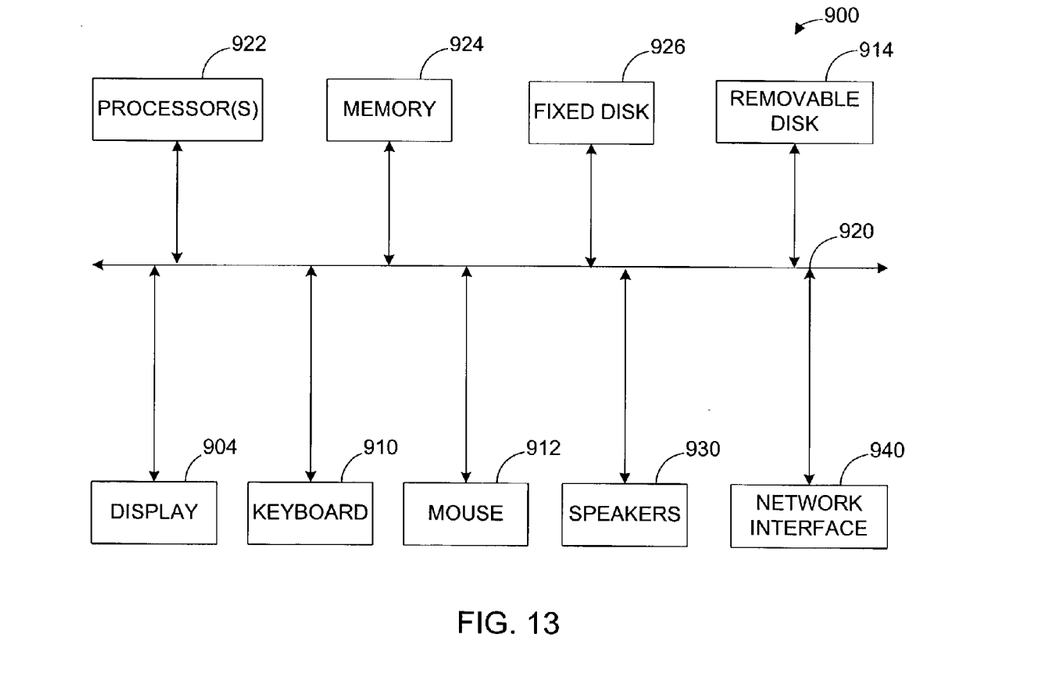

FIGS. 12 and 13 illustrate a computer system 900 suitable for implementing embodiments of the present invention. FIG. 12 shows one possible physical form of the computer system. Of course, the computer system may have many physical forms ranging from an integrated circuit, a printed circuit board and a small handheld device up to a huge super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 13 is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary storage medium (such as a hard disk) that is slower than primary storage. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher-level code that are executed by a computer using an interpreter.

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. An electron beam apparatus for inspecting a semiconductor specimen comprising:
   an electron beam device that is operable to direct an electron beam onto the semiconductor specimen thereby causing electrons to emanate from the semiconductor specimen;
   an electron beam column having a central axis, wherein the electron beam travels along the central axis until the electron beam becomes incident with the specimen;
   a first quadrapole set around the central axis and below the electron beam device, the first quadrapole configured to deflect the electron beam away from the central axis;
   a second quadrapole set around the central axis and below the first quadrapole, the second quadrapole configured to deflect the electron beam towards the central axis such that the electron beam is incident upon a designated area on the specimen regardless of the incident angle of the electron beam,
   wherein the first and the second quadrapoles deflect the electron beam such that the electron beam becomes incident upon the designated area at three or more different incident angles;
   a magnetic lens set around the central axis and located below the second quadrapole, the magnetic lens configured to focus the electron beam upon the specimen; and
   one or more detectors that are positioned above the semiconductor specimen and are configured to collect electrons emanating from the semiconductor specimen in response to the incident beam at the three or more incident angles, wherein the one or more detectors output data signals that correspond to the electrons collected by the detector; and
   an analysis module that is operable to receive the data signals from the detector, correlate the data signals, and construct a three dimensional image of the semiconductor specimen based on the electrons emanating from the specimen in response to the incident beam that is deflected at the three or more incident angles.

2. An electron beam apparatus as recited in claim 1 wherein each of the first and second quadrapole set include two sets of opposing electrostatic or magnetic deflectors.

3. An electron beam apparatus as recited in claim 2 wherein each set of deflectors within each of the first and second quadrapole set are configured to impose deflecting forces upon the electron beam in orthogonal directions.

4. An electron beam apparatus as recited in claim 1 further comprising:
   a stationary specimen stage that secures the specimen.

5. An electron beam apparatus as recited in claim 1 wherein the electron beam apparatus is a critical dimension scanning electron microscope.

6. An apparatus as recited in claim 1 further comprising a plurality of detectors that are each positioned at a unique angular orientation with respect to the semiconductor specimen.

7. A method for inspecting the surface of a semiconductor specimen, the method comprising:
   directing an electron beam along a central axis and towards the semiconductor specimen;
   securing the semiconductor specimen in a stationary position;
   deflecting the electron beam away from the central axis using a first quadrapole set around the central axis;
   deflecting the electron beam back towards the central axis using a second quadrapole set around the central axis and below the first quadrapole set such that the electron beam is incident within a specific area on the semiconductor specimen at three or more different incident angles; and
   constructing a three dimensional image based on electrons collected from the sample in response to the incident beam deflected at the three or more incident angles.

8. A method as recited in claim 7 wherein the deflecting operations are performed by charging opposing deflectors with oppositely charged voltages.

9. A method as recited in claim 7 further comprising:
   focusing the electron beam with a magnetic lens so that the electron beam is focused upon the specific area on the semiconductor specimen.

10. A method as recited in claim 7, wherein
    the electron beam is successively deflected away and towards the central axis such that the electron beam is incident with the specific area on the semiconductor specimen at the three or more incident angles.

11. An electron beam apparatus as recited in claim 1, wherein the analysis module is operable to construct the tree dimensional image using a computer vision reconstruction technique.

12. A method as recited in claim 7, wherein the three-dimensional image is constructed using a computer vision reconstruction technique.

* * * * *

UNITED STATES PATENT AND TRADEMARK OFFICE
CERTIFICATE OF CORRECTION

PATENT NO. : 6,930,308 B1
DATED : August 16, 2005
INVENTOR(S) : Lorusso et al.

It is certified that error appears in the above-identified patent and that said Letters Patent is hereby corrected as shown below:

Column 12,
Line 16, change "the tree" to -- the three --.

Signed and Sealed this

Third Day of January, 2006

JON W. DUDAS
*Director of the United States Patent and Trademark Office*